(12) United States Patent
Welch et al.

(10) Patent No.: US 6,590,655 B2
(45) Date of Patent: Jul. 8, 2003

(54) SYSTEM AND METHOD OF IMPROVING ELECTROMAGNETIC RADIATION BEAM CHARACTERISTICS IN ELLIPSOMETER AND THE LIKE SYSTEMS

(75) Inventors: James D. Welch, Omaha, NE (US); Blaine D. Johs, Lincoln, NE (US); Martin M. Liphardt, Lincoln, NE (US); Ping He, Lincoln, NE (US)

(73) Assignee: J.A. Woollam Co. Inc., Lincoln, NE (US)

( * ) Notice: Subject to any disclaimer, the term of this patent is extended or adjusted under 35 U.S.C. 154(b) by 102 days.

(21) Appl. No.: 09/840,483

(22) Filed: Apr. 23, 2001

(65) Prior Publication Data

US 2001/0033377 A1 Oct. 25, 2001

Related U.S. Application Data

(60) Provisional application No. 60/201,847, filed on Apr. 25, 2000.

(51) Int. Cl.$^7$ .............................. G01J 4/00; G01J 3/28; G01N 21/00; G01N 21/55
(52) U.S. Cl. ...................... 356/369; 356/73; 356/326; 356/445
(58) Field of Search .................... 356/73, 326, 369, 356/445, 446; 250/559.46

(56) References Cited

U.S. PATENT DOCUMENTS

| | | | | |
|---|---|---|---|---|
| 4,175,864 A | * | 11/1979 | Gilby | 356/326 |
| 4,815,858 A | * | 3/1989 | Snail | 356/446 |
| 5,032,734 A | * | 7/1991 | Orazio, Jr. et al. | 250/559.46 |
| 5,414,559 A | | 5/1995 | Burghardt et al. | 359/623 |
| 5,608,526 A | | 3/1997 | Piwonka-Corle et al. | 356/369 |
| 5,796,521 A | | 8/1998 | Kahlert et al. | 359/619 |
| 5,859,424 A | | 1/1999 | Norton et al. | 250/226 |
| 5,889,593 A | * | 3/1999 | Bareket | 356/445 |
| 5,910,842 A | | 6/1999 | Piwonka-Corle et al. | 356/369 |
| 5,917,594 A | | 6/1999 | Norton | 356/327 |
| 6,184,984 B1 | | 2/2001 | Lee et al. | 356/369 |
| 6,384,916 B1 | * | 5/2002 | Furtak | 356/369 |

* cited by examiner

*Primary Examiner*—Georgia Epps
*Assistant Examiner*—Gary O'Neill
(74) *Attorney, Agent, or Firm*—James D. Welch

(57) ABSTRACT

Disclosed are systems for, and methods of controlling radial energy density profiles in, and/or cross-section dimensioning of electromagnetic beams in polarimeters, ellipsometers, reflectometers and spectrophotometers.

22 Claims, 4 Drawing Sheets

SYSTEM AND METHOD OF IMPROVING ELECTROMAGNETIC RADIATION BEAM CHARACTERISTICS IN ELLIPSOMETER AND THE LIKE SYSTEMS

The Application is a CIP of Provisional Application Ser. No. 60/201,847 filed Apr. 25, 2000.

TECHNICAL FIELD

The present invention relates to polarimetry, ellipsometry, reflectometry, spectrophotometry and the like, and more particulalry to systems for, and methods of controlling radial energy density profiles in, and/or cross-sectional dimensioning of electromagnetic beams.

BACKGROUND

It is well known that polarimeter, ellipsometer and spectrophotometer, (often reflectometers as well), and the like systems generally involve causing an electromagnetic beam to non-destructively impinge upon the surface of a sample system along a locus removed from a normal to said sample system surface. Such oblique angles of incidence, it is noted, cause a beam of electromagnetic radiation which is initially essentially circular in cross-section, to form an essentially elliptically shaped "spot" on a sample system surface whereat impingement occurs. Further, it is known that electromagnetic beams provided by typically available sources thereof, generally do not present with radially uniform energy density, but instead have a peak energy density centrally located, which decreases radially. In addition, it has been determined that often said energy density does not decrease in a simple manner such as, for instance, linearly or as a square of increasing radius all the way to zero, but rather upon so decreasing to approximately ten percent (10%) of maximum, "oscilations" as a function of increasing radius occur, much like those seen in the Fourier Transform of a Square Wave. It is noted that the presence of said "oscillations" cause trouble in analysis of ellipsometric data obtained via use of electromagnetic beams which contain them.

While it is also known to apply optical elements, (eg. lenses), which have spherical and aspherical surfaces, (but characterized by radial symmetry), in reflectometer, spectrophotometer, polarimeter, ellipsometer and the like systems, said optical elements generally do not serve specifically to change a spot shape, where an electromagnetic beam impinges on a sample system surface, to substantially circular. It is also known to apply optical elements with other than radial symetry in ellipsometer systems, however, typical application thereof is to enter compensation for various aberational effect. An example of this is discussed in U.S. Pat. No. 5,608,526 to Piwonka-Corle et al.

Additional known Patents include U.S. Pat. No. 5,859,424 to Norton et al. which discloses use of an apodizing filter used to reeuce spot size in optical measurements. U.S. Pat. No. 5,910,842 to Piwonka-Corle et al. is disclosed as it describes application of an elliptically shaped mirror in an ellipsometer system, which elliptically shaped mirror is applied to reduce off-axis aberations. U.S. Pat. No. 5,917,594 to Norton describes application of spherical mirrors in spectroscopic measurement systems. U.S. Pat. No. 6,184,984 to Lee et al. describes application of an off-axis paraboloid mirror in a system for measuring properties of a sample.

A Patent to Burghardt et al., U.S. Pat. No. 5,414,559 is also disclosed as it describes a device for homogenizing a light beam. In addition, U.S. Pat. No. 5,796,521 to Kahlert et al. is disclosed as it describes optical apparatus for homogenizing electromagentic beams which comprises cylindrical lenses.

Utility would be inherrant in a system, and method of its application which would tailor electromagnetic beams so that they present with substantially radially uniform energy density, and/or which would cause a spot at the surface of a sample system whereupon impingement thereof occurs, to be essentially circular.

A need is identified for systems and methods which provide electromagnetic beams in polarimeter, ellipsometer, reflectometer, spectrophotometer and the like systems that present with essentially radially uniform energy density content and/or other than essentially circular cross-sectional shape before they impinge on a sample system surface.

DISCLOSURE OF THE INVENTION

The present invention can be considered to, in the context of application in reflectometer, spectrophotometer, polarimeter and ellipsometer and the like systems, variously apply or combine and apply selections from the group:

means for effecting cross-sectional, substantially radially uniform energy density in electromagnetic beams; and means for effecting desired electromagnetic beam spot shape whereat impingement upon a surface of a sample system occurs.

The means for effecting cross-sectional, substantially radially uniform energy density in electromagnetic beams comprises a sequential combination of a beam expander, a first beam collimator, at least one multi-faceted optical element, a beam condenser and a second beam collimator. Multi-faceted elements can be considered to be comprised of a plurality of small lenses or, for instance, can be constructed from a plurality of half circular, (in cross-section), longitudinal elements aligned parallel to one another; directly adjacent to a second plurality of half circular, (in cross-section), longitudinal elements aligned parallel to one another, wherein the longitudinal orientations of the first and second plurality of half circular, (in cross-section), longitudinal elements are oriented other than parallel, (eg. at an angle of 90 degrees), to one another.

In use an electromagnetic beam with an arbitrary cross-sectional energy density profile is caused to enter said beam expander which serves to expand the beam diameter, then said expanded diameter beam is collimated and caused pass through said at least one multi-faceted optical element which can be thought of as serving to form a multiplicity of spatially separated images of portions of said expanded beam. The beam condensor next serves to focus said spatially separated images atop one another, with the second beam collimator then serving to provide an electromagnetic beam of more uniform radial energy density than was demonstrated by the input beam. A plurality of such multi-faceted optical elements can be sequentially present adjacent to one another to provide further improved uniform radial energy density. And, it is to be understood, where a plurality of multi-faceted optical elements are present, to reduce dispersion effects, they can be constructed of different materials, which different materials which have different wavelength transmission characteristics, and/or specularly dependent indicies of refraction.

The means for effecting desired electromagnetic beam spot shape, whereat impingement on a surface of a sample system occurs, can comprise selection from the group:

lenses which present with non-radial symmetry, (eg. astigmatic/toroidal lenses);

focusing mirrors with non-radial symetry, (eg. parabolic mirrors); and apertrues with non-radial symetry:

where the terminology "non-radial symetry" is to be interpreted to mean, for instance, that a "width-wise" dimension is different from an orthogonally oriented "length-wise" dimension. That is there is an aspect ratio offset from 1.0. Application of non-radial symetry optical elements can result in a circular cross-section electromagnetic beam becomming shaped into an elliptical beam of electromagnetic radiation. The purpose of this is to, in combination with a "length-wise" elongating effect on the beam, which results from its non-normal oblique angle of incidence on the surface of a sample system, result in an essentially circular beam spot shape at the location where it impinges on the surface of said sample system.

Of course, it is within the scope of the present invention to combine the effects of non-radial symetry aperture and/or non-radial symetry lenses and/or non-radial symetry focusing mirrors to effect essentially circular beam spot shape at the location whereat impingement on the surface of a sample system occurs. Further, any of the identified beam shaping optical elements can be combined with the means for effecting cross-sectional, essentially radially uniform energy density in electromagnetic beams, and such combinations provide a preferred embodiment.

More precisely the present invention is then a reflectometer, spectrophotometer, polarimeter or ellipsometer system for application in non-destructive investigation of sample systems, comprising:

source of electromagnetic radiation, means for effecting cross-sectional, essentially radially uniform energy density in electromagnetic beams, said means for effecting cross-sectional, essentially radially uniform energy density in electromagnetic beams comprising a sequential combination of:

beam expander;

first beam collimator;

at least one multi-faceted optical element;

beam condenser; and second beam collimator;

stage for supporting a sample system, and detector;

such that in use electromagnetic radiation of arbitrary cross-sectional radial energy density is provided by said source of electromagnetic radiation and is caused to pass through said means for effecting cross-sectional, essentially radially uniform energy density in electromagnetic beams such that a beam of substantially radially uniform energy density is output therefrom, is caused to interact with a sample system placed on said stage for supporting a sample system, and then enter said detector. The present invention reflectometer, spectrophotometer, polarimeter or ellipsometer system can also comprise at least one selection from the group consisting of:

lens which presents with non-radial symmetry;

focusing mirror with non-radial symetry; and apertrues with non-radial symetry:

positioned between said means for effecting cross-sectional, essentially radially uniform energy density in electromagnetic beams, and said stage for supporting a sample system; such that said beam of electromagnetic radiation which impinges on said sample system, first interacts therewith to the end that an essentially circular shaped spot is effected upon the surface of aid sample system.

Additionally, the present invention system can comprise, a reflectometer, spectrophotometer, polarimeter or ellipsometer system for application in non-destructive investigation of sample systems which sequentially comprises a source of electromagnetic radiation, an optical element which demonstrates non-radial symetry, a stage for supporting a sample system, and a detector, such that a beam of electromagnetic radiation provided by said source of electromagnetic radiation is caused to interact with said optical element which demonstrates non-radial symetry and then impinge on a surface of a sample system placed on said stage for supporting a sample system, threat forming an essentially circular spot, said beam of electromagnetic radiation then being caused to enter said detector. Said optical element can be a lens which presents with non-radial symmetry; a focusing mirror with non-radial symetry; and apertrues with non-radial symetry.

The reflectometer, spectrophotometer, polarimeter or ellipsometer system can further comprise a polarizer between said means for effecting cross-sectional, essentially radially uniform energy density in electromagnetic beams, and said stage for supporting a sample system, the purpose thereof being to cause a state of polarization on a beam of electromagnetic radiation caused to pass therethrough. Further, where a polarizer is included, an analyzer is typically included between the stage for supporting a sample system and the detector.

A present invention method of non-destructively analyzing a sample system in a reflectometer, spectrophotometer, polarimeter or ellipsometer system comprises:

a. providing a reflectometer, spectrophotometer, polarimeter or ellipsometer system as described;

b. placing a sample system on said stage for supporting a sample system;

c. causing said source of electromagnetic radiation to perform at least one selection from the group:

a. provide a beam of electromagnetic radiation of arbitrary cross-sectional radial energy density and causing it to pass through said means for effecting cross-sectional, essentially radially uniform energy density in electromagnetic beams such that a beam of substantially radially uniform energy density is output therefrom, is caused to impinge at an oblique angle upon, and interact with a sample system placed on said stage for supporting a sample system, and then enter said detector; or b. provide a beam of electromagnetic radiation provided by said source of electromagnetic radiation is caused to interact with optical element(s) which demonstrates non-radial symetry and then impinge on a surface of a sample system placed on said stage for supporting a sample system, threat forming an essentially circular spot, said beam of electromagnetic radiation then being caused to enter said detector, said optical element(s) being a lens which presents with non-radial symmetry and/or a focusing mirror with non-radial symetry and/or apertrues with non-radial symetry.

The present invention will be better understood by reference to the Detailed Description of the Invention Section of this Specification, in conjunction with the Drawings.

SUMMARY OF THE INVENTION

It is therefore a primary objective and/or purpose of the present invention to teach, in the context of reflectometer, spectrophotometer, polarimeter, ellipsometer and the like systems, application of means for effecting cross-sectional, essentially radially uniform energy density in electromagnetic beams.

It is another objective and/or purpose of the present invention to teach, in the context of reflectometer, spectrophotometer, polarimeter, ellipsometer and the like systems, application of optical element(s) which demonstrate non-radial symetry, for the purpose of causing a beam of electromagnetic radiation to form an essentially circular shaped spot upon the surface of a sample system, whereupon it impinges.

It is yet another objective and/or purpose of the present invention to teach, in the context of reflectometer, spectrophotometer, polarimeter, ellipsometer and the like systems, application of means for effecting cross-sectional, essentially radially uniform energy density in electromagnetic beams, in functional combination with application of optical element(s) which demonstrates non-radial symmetry, for the purpose of causing a beam of electromagnetic radiation to form an essentially circular shaped spot upon the surface of a sample system, whereupon it impinges.

Other objectives and/or purposes of the present invention will become apparent upon a reading of the Specification and Claims.

BRIEF DESCRIPTION OF THE DRAWINGS

FIG. 3c1 demonstrates, in perspective, a Reflective Mirror (RM) with non-radial symetry.

FIG. 3c2 shows said Reflective Mirror (RM) of FIG. 3c1 in side cross-sectional.

FIG. 6b1 demonstrates a Beam of Electromagnetic Radiation of substantially uniform radial energy density (EMO) at location "B" in FIG. 5.

FIG. 6b2 demonstrates that the Beam of Electromagnetic Radiation of substantially uniform radial energy density (EMO) at point B in FIG. 5 is of essentially circular cross-sectional dimensions.

FIG. 8b1 shows an Essentially Uniform Radial Energy Density Electromagnetic Beam Profile which appears at Point "B" in FIG. 7.

FIG. 8b2 demonstrates that the Essentially Uniform Radial Energy Density Electromagnetic Beam at said Point "B" in FIG. 7 is of essentially circular cross-sectional dimensions.

DETAILED DESCRIPTION

Figure 1:
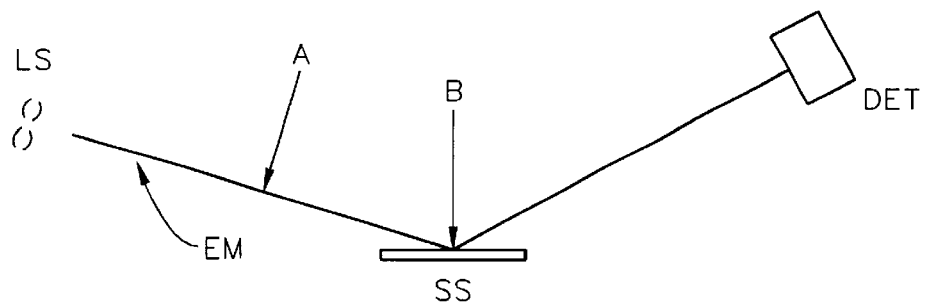
FIG. 1 a general representation of a Source of Electromagnetic Radiation (LS) which provides a Beam of Electromagnetic Radiation (EM), and a Detector (DET). The Beam of Electromagnetic Radiation (EM) is shown to impinge on a Sample System (SS) at an oblique Angle.
Figure 2A:
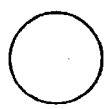
FIG. 2a shows that a Beam of Electromagnetic Radiation (EM) typically presents with a circular cross-section at Point A in FIG. 1.
Figure 2B:
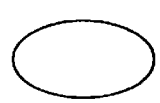
FIG. 2b demonstrates that said circular cross-section results in an essentially elliptical spot shape occuring at the Point B of impingement on the Sample System (SS), as viewed from above.

Turning now to the Drawings, there is shown in FIG. 1 a general representation of a Source of Electromagnetic Radiation (LS) which provides a Beam of Electromagnetic Radiation (EM), and a Detector (DET). The Beam of Electromagnetic Radiation (EM) is shown to impinge on a Sample System (SS) at an oblique Angle. FIG. 2a shows that a Beam of Electromagnetic Radiation (EM) typically presents with a circular cross-section at Point A in FIG. 1, and FIG. 2b demonstrates that said circular cross-section results in an essentially elliptical spot shape occuring at the point of impingement, (ie. Point B in FIG. 1) on the Sample System (SS), as viewed from above.

Figure 2C:
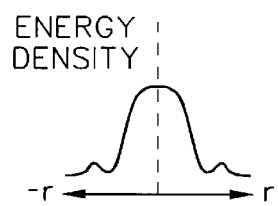
FIG. 2c demonstrates that a Beam of Electromagnetic Radiation (EM) typically presents with a non-uniform radial Energy Density, for instance at Point A in FIG. 1.

FIG. 2c demonstrates that a Beam of Electromagnetic Radiation (EM) typically presents with a non-uniform radial Energy Density, for instance at Point A in FIG. 1.

Figure 3A:
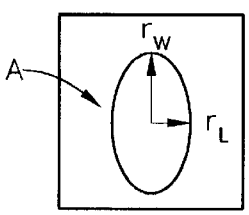
FIG. 3a demonstrates a non-circular aperture with a "width-wise" radius being larger than a "length-wise" radius.
Figure 3B:
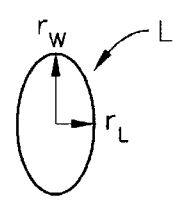
FIG. 3b demonstrates a lens (L) with non-radial symetry.

FIGS. 3a–3c demonstrate Optical Elements with non-radial symetry. As will become clear,.placing such an Optical Element so that it interacts with a cross-sectional circular shaped Beam of Electromagnetic Radiation prior to the Sample System (SS) causes it to assume an essentially cross-sectional elliptical shaped Beam of Electromagnetic Radiation. FIG. 3a demonstrates a non-circular aperture with a "width-wise" radius being larger than a "length-wise" radius. FIG. 3b demonstrates a lens (L) with non-radial symetry and FIG. 3c 1 demonstrates, in perspective, a Reflective Mirror (RM) with non-radial symetry, and FIG. 3c2 shows said Reflective Mirror (RM) of FIG. 3c1 in side cross-sectional.

Figure 4A:
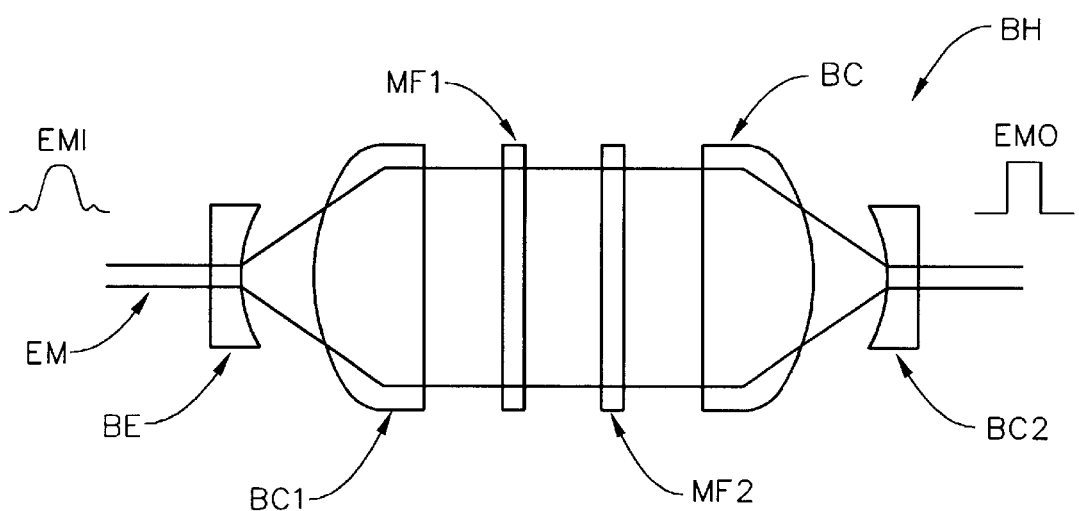
FIG. 4a shows a means (BH) for effecting cross-sectional, essentially radially uniform energy density in electromagnetic beams.

FIG. 4a shows a means (BH) for effecting cross-sectional, essentially radially uniform energy density in electromagnetic beams. Shown a sequential combination of:

Beam Expander (BE);
First Beam Collimator (BC1);
at least one Multi-Faceted Optical Element (MF1) (MF2);
Beam Condenser (BC); and
Second Beam Collimator (BC2).

Figure 4B:
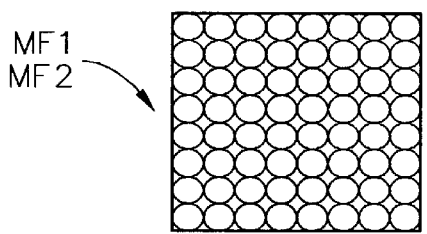
FIG. 4b demonstrates, in frontal view, that the at least one Multi-Faceted Optical Element(s) (MF1) (MF2) shown in side view in FIG. 4a, can comprise a lens with a multiplicity of small lenses distributed therewithin.
Figure 4C:
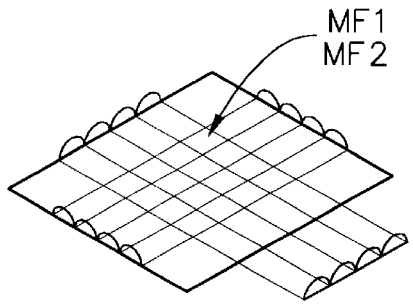
FIG. 4c shows in perspective that such Multi-Faceted Optical Element(s) (MF1) (MF2) can be fabricated as constructed from a plurality of half circular, (in cross-section), longitudinal elements aligned parallel to one another; directly adjacent to a second plurality of half circular, (in cross-section), longitudinal elements oriented other than parallel to the first said plurality of half circular longitudinal elements.

The effect of passing a Beam of Electromagnetic Radiation (EM) of arbitrary input radial Energy Density (EM1) is to produce a more uniform radial Energy Density (EMO) as output. FIG. 4b demonstrates, in frontal view, that the at least one Multi-Faceted Optical. Element(s) (MF1) (MF2) shown in side view in FIG. 4a, can comprise a lens with a multiplicity of small lenses distributed therewithin. FIG. 4c shows in perspective that such Multi-Faceted Optical Element(s) (MF1) (MF2) can be fabricated as constructed from a plurality of half circular, (in cross-section), longitudinal elements aligned parallel to one another; directly adjacent to a second plurality of half circular, (in cross-section), longitudinal elements aligned parallel to one another, wherein the longitudinal orientations of the first and second plurality of half circular, (in cross-section), longitudinal elements are oriented other than parallel, (eg. at an angle of 90 degrees), to one another. (Note, the longitudinal elements need not be strictly half circular in cross-section, but can include half elliptical etc.).

In use the Multi-Faceted Optical Element(s) (MF1) (MF2) produce a multilipcity of images, each thereof being a portion of an Electromagnetic Beam (EM) which presents with energy density (EMI) produced by the Beam Expander (BE). The Beam Condensor (BC) then superimposes said multiplicty of images into a focused small area, which focused small area is collimated by Second Beam Collimator (BC2) into Output Electromagnetic Beam (EMO), which Output Electromagnetic Beam has a more radially uniform energy density (EMO) distribution than did the input Electromagnetic Beam (EMI).

Figure 3D:
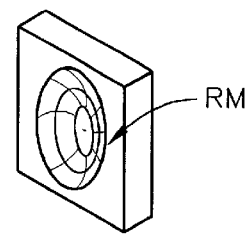
FIG. 3D demonstrates that a lens can be of multi-element construction to achieve quasi-achromatic characteristics.
Figure 3D:
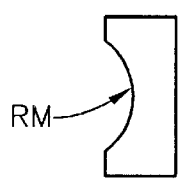
Figure 3D:
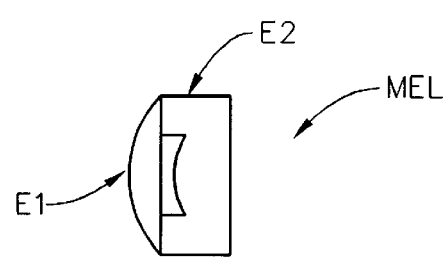
Figure 5:
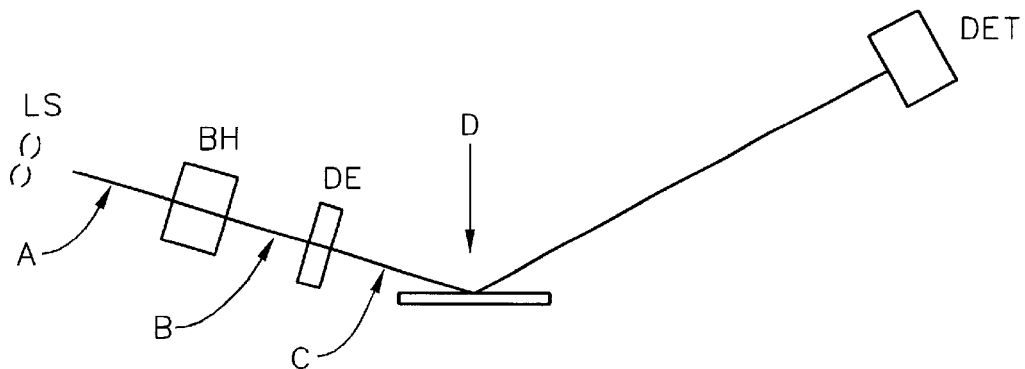
FIG. 5 demonstrates a present invention reflectometer, spectrophotometer, polarimeter or ellipsometer system.
Figure 6A:
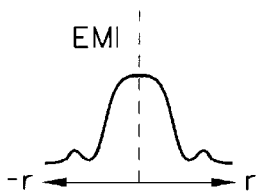
FIG. 6a demonstrates a Beam of Electromagnetic Radiation of arbitrary radial energy density (EMI) at location "A" in FIG. 5.
Figure 6C:
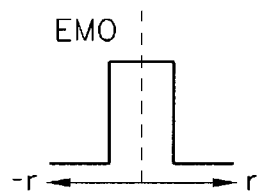
FIG. 6c demonstrates the effect of the Optical Element (OL) on the cross-sectional shape of the Beam of Electromagnetic Radiation of substantially uniform radial energy density (EMO) at location "B".
Figure 6C:
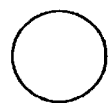
Figure 6C:
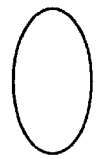
Figure 6D:
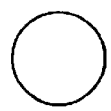
FIG. 6d demonstrates that a Beam of Electromagnetic Radiation with cross-sectional dimensions as demonstrated in FIG. 6c forms a substantially circular shaped spot at the Point of Impingement (see Point "D" in FIG. 5), upon the Sample System.
Figure 9:
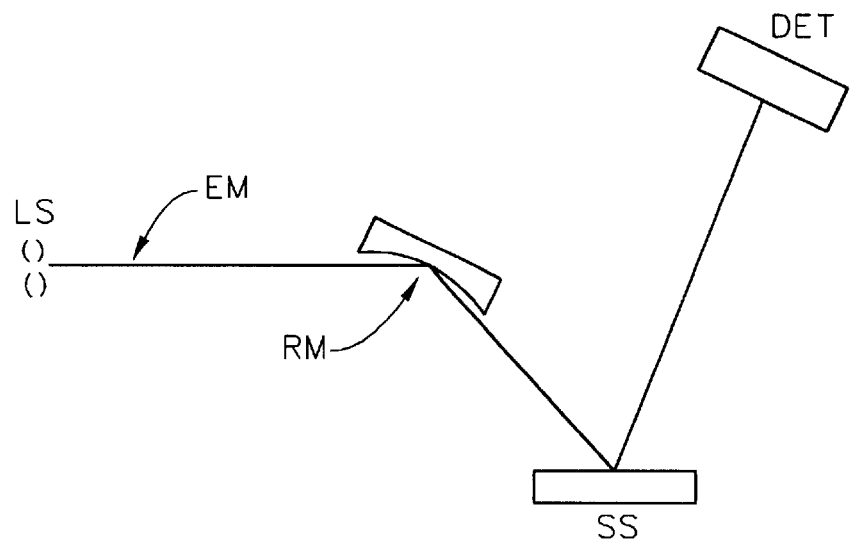
FIG. 9 shows a Reflective Mirror (RM) with non-radial symetry, as shown in FIGS. 3c1 and 3c2, which can be applied in place of the transmissive Optical Elements described with respect to FIG. 5.

FIG. 5 demonstrates a present invention reflectometer, spectrophotometer, polarimeter or ellipsometer system comprising a Source of electromagnetic Radiation (LS) a Means (BH) for effecting cross-sectional, essentially radially uniform energy density in electromagnetic beams (BH), and Optical Element (OE), a Sample System (SS) and a Detector (DET). FIG. 6a demonstrates a Beam of Electromagnetic Radiation of arbitrary radial energy density (EMI) at location "A" in FIG. 5. FIG. 6b1 demonstrates a Beam of Electromagnetic Radiation of substantially uniform radial energy density (EMO) at location "B" in FIG. 5. FIG. 6b2 demonstrates that the Beam of Electromagnetic Radiation of substantially uniform radial energy density (EMO) at point B in FIG. 5 is of essentially circular cross-sectional dimensions. FIG. 6c demonstrates the effect of the Optical Element (OL) on the cross-sectional shape of the Beam of Electromagnetic Radiation of substantially uniform radial energy density (EMO) at location "B". Note that said Optical Element (OL) can be a FIG. 3a non-circular aperture with a "width-wise" radius being larger than a "length-wise" radius, or a FIG. 3b lens (L) with non-radial symetry. FIG. 6d demonstrates that a Beam of Electromagnetic Radiation with cross-sectional dimensions as demonstrated in FIG. 6c forms a substantially circular shaped spot at the Point of Impingement (see Point "D" in FIG. 5), upon the Sample System. FIG. 9 demonstrates that a Reflective Mirror (RM) with non-radial symetry, as shown in FIGS. 3c1 and 3c2, can be applied in place of the transmissive Optical Elements, described with respect to FIG. 5, (ie. the FIG. 3a non-circular aperture with a "width-wise" radius being larger than a "length-wise" radius or the FIG. 3b lens (L) with non-radial symetry). FIG. 3d is included to indicate that lense can be comprised of multi-elements. Multi-element lenses can be of benefit where it is desired to acheive quasi-achromatic charactristics.

Figure 7:
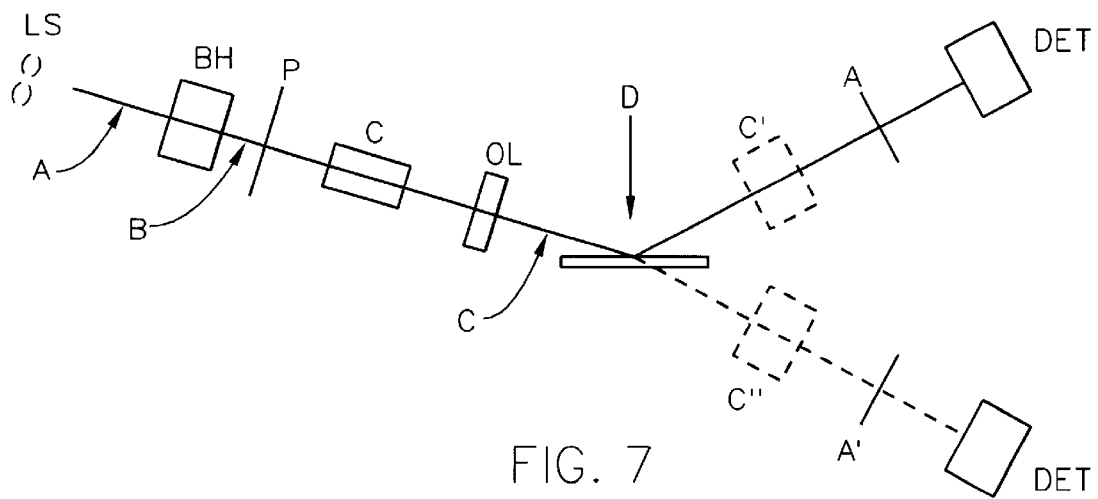
FIG. 7 demonstrates a present invention ellipsometer system, which ellipsometer system is much like that described with respect to FIG. 5, but note that a Polarizer (P), optional Compenator (C), (C') (C"), and with an Analyzer (A) (A') are present. Both Reflective and Transmissive Sample System scenarios are demonstrated.

FIG. 7 demonstrates a present invention ellipsometer system, which ellipsometer system is much like that described with respect to FIG. 5, but note that a Polarizer (P), optional Compenator (C), (C') (C"), and with an Analyzer (A) (A') are present. Note also that both Reflective and Transmissive Sample System scenarios are demonstrated.

Figure 8A:
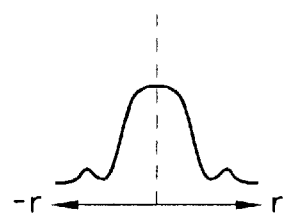
FIG. 8a shows an arbitrary radial energy density Electromagnetic Beam profile present at Point "A" in FIG. 7, as provided by a typical Source of Electromagnetic Radiation (LS).
Figure 8C:
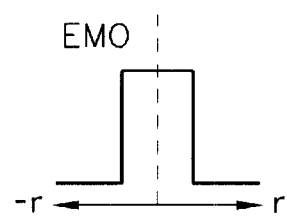
FIG. 8c demonstrates that the Electromagnetic Beam Profile which appears at Point "C" in FIG. 7, after passing through the optical Element (OL), with non-radial symetry is of an elliptical-like shape in cross-section.
Figure 8C:
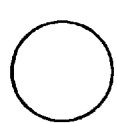
Figure 8C:

FIG. 8a shows an arbitrary radial energy density Electromagnetic Beam profile present at Point "A" in FIG. 7, as provided by a typical Source of Electromagnetic Radiation (LS). FIG. 8b1 shows an Essentially Uniform Radial Energy Density Electromagnetic Beam Profile which appears at Point "B" in FIG. 7. FIG. 8b2 demonstrates that the Essentially Uniform Radial Energy Density Electromagnetic Beam at said Point "B" in FIG. 7 is of essentially circular cross-sectional dimensions. FIG. 8c demonstrates that the Electromagnetic Beam Profile which appears at Point "C" in FIG. 7, after passing through the Optical Element (OL), with non-radial symetry is of an elliptical-like shape in cross-section. FIG. 8b2 also can be taken to show that the spot shape looking down in FIG. 7, where the Electromagnetic Beam impinges on the Sample System (SS), (ie. at Point "D"), is essentially circular. Again, the oblique Angle-Of-Incidence causes elongation of the Electromagnetic Beam shape shown in FIG. 8c, so that. at point "D" in FIG. 7 an essentially circular spot is achieved.

It is specifically noted that the present invention can be practiced in the context of reflectometer, spectrophotometer, polarimeter or ellipsometer systems. Typically, reflectometers and spectrophotometers are distinguished from ellipometers and polarimeters in that they lack polarization effecting and/or detecting means such as, respectfully, Polarizer and Analyzer means. Further, while reflectometers utilize unpolarized electromagentic beams oriented to impinge on, and reflect from, a sample system surface at a close to normal angle of incidence, spectrophotmeters utilize electromagnetic beams oriented at any angle to the surface of a sample system, and can involve detection of reflected or transmitted beams.

It is noted that the terminology "non-radial symetry" is used herein to identify an optical element with radial dimensions which are different in, for instance, orthogonal directions.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A reflectometer, spectrophotometer, polarimeter or ellipsometer system for application in non-destructive investigation of sample systems, comprising:

source of electromagnetic radiation;
means for effecting cross-sectional, essentially radially uniform energy density in electromagnetic beams, said means for effecting cross-sectional, essentially radially uniform energy density in electromagnetic beams comprising a sequential combination of:
  beam expander;
  first beam collimator;
  at least one multi-faceted optical element;
  beam condenser; and
  second beam collimator;
stage for supporting a sample system; and
detector;
such that in use electromagnetic radiation of arbitrary cross-sectional radial energy density is provided by said source of electromagnetic radiation and is caused to pass through said means for effecting cross-sectional, essentially radially uniform energy density in electromagnetic beams such that a beam of substantially radially uniform energy density is output therefrom, is caused to approach at other than a normal angle to a surface of, and interact with a sample system placed on said stage for supporting a sample system, and then enter said detector.

2. A reflectometer, spectrophotometer, polarimeter or ellipsometer system as in claim 1, which further comprises a polarizer between said means for effecting cross-sectional, essentially radially uniform energy density in electromagnetic beams, and said stage for supporting a sample system, the purpose thereof being to cause a state of polarization on a beam of electromagnetic radiation caused to pass therethrough.

3. A reflectometer, spectrophotometer, polarimeter or ellipsometer system as in claim 1, which further comprises at least one selection from the group consisting of:
  lens which presents with non-radial symmetry;
  focusing mirror with non-radial symetry; and
  apertrues with non-radial symetry:
positioned between said means for effecting cross-sectional, essentially radially uniform energy density in electromagnetic beams, and said stage for supporting a sample system;
such that said beam of electromagnetic radiation which impinges on said sample system, first interacts therewith to the end that an essentially circular shaped spot is effected upon the surface of said sample system.

4. A reflectometer, spectrophotometer, polarimeter or ellipsometer system as in claim 2, which further comprises at least one selection from the group consisting of:
  lens which presents with non-radial symmetry;
  focusing mirror with non-radial symetry; and
  apertrues with non-radial symetry:
positioned between said means for effecting cross-sectional, essentially radially uniform energy density in electromagnetic beams, and said stage for supporting a sample system;
such that said beam of electromagnetic radiation which impinges on said sample system after interacting therewith causes an essentially circular shaped spot upon the surface of said sample system.

5. A method of non-destructively analyzing a sample system comprising the steps of:
  a. providing a reflectometer, spectrophotometer, polarimeter or ellipsometer system comprising:
    source of electromagnetic radiation,
    stage for supporting a sample system, and
    detector;
  such that in use a beam of electromagnetic radiation is provided by said source of electromagnetic radiation, is caused to interact with a sample system placed on said stage for supporting a sample system, and enter said detector;
  b. positioning, between said source of electromagnetic radiation and said stage for supporting a sample system, a means for effecting cross-sectional, essentially radially uniform energy density in electromagnetic beams, said means for effecting cross-sectional, essentially radially uniform energy density in electromagnetic beams comprising a sequential combination of:
    beam expander;
    first beam collimator;
    at least one multi-faceted optical element;
    beam condenser; and
    second beam collimator;
  c. placing a sample system on said stage for supporting a sample system;
  d. causing said source of electromagnetic radiation to provide a beam of electromagnetic radiation of arbitrary cross-sectional radial energy density and causing it to pass through said means for effecting cross-sectional, essentially radially uniform energy density in electromagnetic beams such that a beam of substantially radially uniform energy density is output therefrom, is caused to impinge at an oblique angle upon, and approach at other than a normal angle to a surface of, and interact with a sample system placed on said stage for supporting a sample system, and then enter said detector.

6. A method of non-destructively analyzing a sample system as in claim 5 which further comprises, in the step of providing a reflectometer, spectrophotometer, polarimeter or ellipsometer system, adding a polarizer between said source of electromagnetic radiation and said stage for supporting a sample system.

7. A method of non-destructively analyzing a sample system as in claim 5 which further comprises, in the step of providing a reflectometer, spectrophotometer, polarimeter or ellipsometer system, adding, between said source of electromagnetic radiation and said stage for supporting a sample system, an optical element selected from the group consisting of:
  lens which presents with non-radial symmetry;
  focusing mirror with non-radial symetry; and
  apertrues with non-radial symetry:
such that said essentially radially uniform energy density electromagnetic beam which is caused to impinge at other than a normal angle upon, and interact with a sample system, interacts with said optical element prior to interacting with said sample system, and is thereby caused to provide an essentially circular spot shape on said sample system at the point of impingement thereupon.

8. A reflectometer, spectrophotometer, polarimeter or ellipsometer system for application in non-destructive investigation of sample systems, sequentially comprising a source of electromagnetic radiation, an optical element which demonstrates non-radial symetry, a stage for supporting a sample system, and a detector, such that a beam of electromagnetic radiation provided by said source of electromagnetic radiation is caused to interact with said optical element which demonstrates non-radial symetry and then impinge on a surface of a sample system placed on said stage for supporting a sample systems, thereat forming an essentially circular spot, said beam of electromagnetic radiation then being caused to enter said detector;
  the improvement being that the beam of electromagnetic radiation provided by said source of electromagnetic radiation is caused to interact with a means for effecting cross-sectional, essentially radially uniform energy density, in addition to interacting with said optical element which demonstrates non-radial symetry.

9. A reflectometer, spectrophotometer, polarimeter or ellipsometer system as in claim 8, in which said optical element is selected from the group consisting of:
   lens which presents with non-radial symmetry;
   focusing mirror with non-radial symetry; and
   apertrues with non-radial symetry.

10. A reflectometer, spectrophotometer, polarimeter or ellipsometer system as in claim 8, which further comprises:
   means for effecting cross-sectional, essentially radially uniform energy density in electromagnetic beams, said means for effecting cross-sectional, essentially radially uniform energy density in electromagnetic beams comprising a sequential combination of:
      beam expander;
      first beam collimator;
      at least one multi-faceted optical element;
      beam condenser; and
      second beam collimator;
   said means for effecting cross-sectional, essentially radially uniform energy density in electromagnetic beams being positioned between said source of electromagnetic radiation and said stage for supporting a sample system.

11. A method of causing an electromagnetic beam to form an essentially circular spot shape at a surface of a sample system, in a reflectometer, spectrophotometer, polarimeter or ellipsometer system; where said electromagnetic beam impinges onto said sample system surface from a source located so as to cause said beam of electromagnetic radiation to approach said sample system along a locus other than coincident with a normal to said sample system surface, comprising the steps of causing a beam of electromagnetic radiation which demonstrates cross-sectional, essentially radially uniform energy density, to progress toward a sample system, and placing an optical element in the pathway of said electromagnetic beam which presents with non-radial symmetry.

12. A method of causing an electromagnetic beam to form an essentially circular spot shape at a surface of a sample system as in claim 11, in which the optical element is selected to be a lens.

13. A method of causing an electromagnetic beam to form an essentially circular spot shape at a surface of a sample system as in claim 12, in which the optical element is a lens is selected to be a multi-element lens.

14. A method of causing an electromagnetic beam with an essentially circular cross-sectional shape to form an essentially circular spot shape at a surface of a sample system as in claim 11, wherein the optical element is an essentially eliptically shaped aperture.

15. A method of causing an electromagnetic beam with an essentially circular cross-sectional shape to form an essentially circular spot shape at a surface of a sample system as in claim 11, wherein the optical element is a focusing mirror with non-radial symetry.

16. A reflectometer, spectrophotometer, polarimeter or ellipsometer system comprising a source of electromagnetic radiation, a means for effecting cross-sectional, essentially radially uniform energy density, a stage for supporting a sample system, and an optical element; said optical element causing a beam of electromagnetic radiation which demonstrates cross-sectional, essentially radially uniform energy density, provided by said source of electromagnetic radiation and said means for effecting cross-sectional, essentially radially uniform energy density, to, prior to the location of said stage for supporting a sample system, present with a cross-sectional shape which is essentially elliptical.

17. A reflectometer, spectrophotometer, polarimeter or ellipsometer system as in claim 16 in which said essentially elliptical beam cross-sectional shape is effected by use of an optical element which comprises an essentially elliptically shaped aperture.

18. A reflectometer, spectrophotometer, polarimeter or ellipsometer system as in claim 16 in which said essentially elliptical beam cross-sectional shape is effected by use of an optical element which comprises a non-radial symetry lens.

19. A reflectometer, spectrophotometer, polarimeter or ellipsometer system as in claim 16 in which said essentially elliptical beam cross-sectional shape is effected by use of an optical element which comprises a non-radial symetry focusing mirror.

20. A method of causing an electromagnetic beam in a reflectometer, spectrophotometer, polarimeter or ellipsometer system, to form an essentially circular spot shape at a surface of a sample system, where said electromagnetic beam impinges onto said sample system surface from a source located so as to cause said beam of electromagnetic radiation to approach said sample system along a locus other than coincident with a normal to said sample system surface, comprising the step of placing an aperture in the pathway of said electromagnetic beam which presents with a larger "width-wise" than "length-wise" dimension, such that the elongation of the electromagnetic beam in the "length-wise" direction at the sample system surface whereat the beam impinges as a result of its impinging along a direction removed from perpendicular thereto, is appropriate to cause the resulting beam spot shape to be essentially circular at said surface of a sample system where said electromagnetic beam impinges onto said sample system surface; said method being characterized by the step of causing said electromagnetic beam to demonstrate cross-sectional, essentially radially uniform energy density.

21. A method of causing an electromagnetic beam in a reflectometer, spectrophotometer, polarimeter or ellipsometer system, to form an essentially circular spot shape at a surface of a sample system as in claim 20, which further comprises the step of placing a second optical element in the pathway of said electromagnetic beam which presents with non-radial symmetry.

22. A method of causing an electromagnetic beam in a reflectometer, spectrophotometer, polarimeter or ellipsometer system, to form an essentially circular spot shape at a surface of a sample system, where said electromagnetic beam impinges onto said sample system surface from a source located so as to cause said beam of electromagnetic radiation to approach said sample system along a locus other than coincident with a normal to said sample system surface, comprising the step of placing an aperture in the pathway of said electromagnetic beam which presents with a larger "width-wise" than "length-wise" dimension, such that the elongation of the electromagnetic beam at the point on the sample system surface whereat the beam impinges thereupon as a result of its impinging along a direction removed from perpendicular thereto causes the spot shape thereat to be more circular than it would otherwise be;
   said method further comprising the step of placing a second optical element in the pathway of said electromagnetic beam which presents with non-radial symmetry;
   the combined result of said aperture which presents with a larger "width-wise" than "length-wise" dimension, and second optical element which presents with non-radial symmetry, being an essentially circular spot shape at said surface of a sample system where said electromagnetic beam impinges thereonto;
   said method being characterized by the step of causing said electromagnetic beam to demonstrate cross-sectional, essentially radially uniform energy density.

* * * * *